United States Patent [19]
de Costa et al.

[11] Patent Number: 5,336,483
[45] Date of Patent: Aug. 9, 1994

[54] RADIOLABELED N-SUBSTITUTED-6-IODO-3,14-DIHYDROXY-4,5α-EPOXYMORPHINANS, INTERMEDIATES FOR PRODUCING THE SAME, AND A PROCESS FOR THE PREPARATION AND METHODS OF DETECTING OPIOID RECEPTORS

[75] Inventors: Brian R. de Costa, Gaithersburg, Md.; Michael J. Iadarola, Washington, D.C.; Kenner C. Rice, Bethesda; Richard B. Rothman, Silver Spring, both of Md.; Karen F. Berman, Washington, D.C.

[73] Assignee: The United States of America as represented by the Department of Health and Human Services, Washington, D.C.

[21] Appl. No.: 3,731

[22] Filed: Jan. 13, 1993

Related U.S. Application Data

[62] Division of Ser. No. 715,762, Jun. 14, 1991, Pat. No. 5,208,338.

[51] Int. Cl.⁵ ............... A61K 49/02; C07D 489/08
[52] U.S. Cl. ..................... 424/1.85; 546/44; 435/29; 436/63; 424/1.45
[58] Field of Search ............ 424/1.1, 1.45, 1.65, 424/1.85; 546/44, 45, 46; 436/57, 63

[56] References Cited

U.S. PATENT DOCUMENTS

| | | | |
|---|---|---|---|
| 3,137,701 | 6/1964 | Ayer | 546/44 |
| 3,254,088 | 5/1966 | Lewenstein | 546/44 |
| 3,332,950 | 7/1967 | Blumberg et al. | 546/44 |
| 4,064,228 | 12/1977 | Gross | 424/1 |
| 4,241,065 | 12/1980 | Boswell, Jr. et al. | 546/46 |
| 4,451,470 | 5/1984 | Ganti | 546/45 X |
| 4,678,779 | 7/1987 | Meyers et al. | 514/178 |
| 4,767,718 | 8/1988 | Meyers | 546/44 X |
| 4,775,759 | 10/1988 | Rice et al. | 546/44 |
| 5,208,338 | 5/1993 | de Costa et al. | 546/44 |

*Primary Examiner*—Richard D. Lovering
*Assistant Examiner*—John M. Covert
*Attorney, Agent, or Firm*—Birch, Stewart, Kolasch & Birch

[57] ABSTRACT

The present invention is directed to radiolabeled N-substituted-6-iodo-3,14-dihydroxy-4,5α-epoxymorphinans, intermediates for producing the same, and a process for the preparation and methods of detecting opioid receptors. The radioimaging agent of the present invention has the following formula:

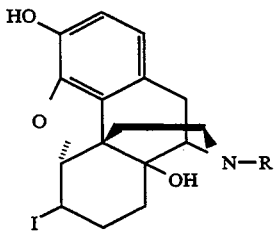

wherein I is selected from the group consisting of $^{123}$I and $^{125}$I; and where R is alkyl, cycloalkylloweralkyl or allyl.

8 Claims, No Drawings

RADIOLABELED N-SUBSTITUTED-6-IODO-3,14-DIHYDROXY-4, 5α-EPOXYMORPHINANS, INTERMEDIATES FOR PRODUCING THE SAME, AND A PROCESS FOR THE PREPARATION AND METHODS OF DETECTING OPIOID RECEPTORS

This application is a divisional of copending application Ser. No. 07/715,762, filed on Jun. 14, 1991, now U.S. Pat No. 5,208,338, the entire contents of which are hereby incorporated by reference.

BACKGROUND OF THE INVENTION

1. Field of the Invention

The present invention is directed to N-substituted-6-iodo-3,14-dihydroxy-4,5-α-epoxymorphinan, intermediates for producing the same, and methods of detecting the presence of opioid receptors.

2. Description of Related Art

Positron Emission Tomography (PET) and Single Photon Emission Computerized Tomography (SPECT) are non-invasive techniques for the direct visualization and quantitation of various parameters of brain function such regional cerebral blood flow and cerebral metabolism. The functional status and anatomical disposition of specific neuroreceptor systems can also be ascertained by the PET and SPECT methods. [$^{18}$F]cyclofoxy was developed as an agent for visualization of opioid receptors with PET. With this compound and PET, abnormalities of opioid receptor distribution in diseased states has been demonstrated. However, while PET is acknowledged as a useful state-of-the-art technique, it suffers substantial disadvantages which include high operating costs of the PET facility (a cyclotron is required), numerous personnel to man the facility, technical complexity of performing PET studies and very short half-lives for all positron emitting isotopes. The short half life of $^{18}$F and other positron emitting radioisotopes precludes their use in ligands which exhibit either a slow "on rate" or slow receptor localization. These and other disadvantages result in inadaptability of the technique to the small hospital setting and greater costs to the patient or third party care-providers.

Many of the problems associated with the short half life of positron emitting isotopes can be circumvented by a technique known as SPECT or single photon emission computerized tomography. SPECT was originally developed to study regional cerebral blood flow and cerebral perfusion and has been especially useful in examining differences in cerebral blood flow seen in Alzheimer's disease and depression. However, it has more recently been adapted to neurotransmitter systems. In SPECT studies, an $^{123}$I-labelled form of a drug or ligand is administered to subjects. $^{123}$I differs from positron emitting ligands in that it emits single monoenergetic x-ray photons, has a longer half life (13.2 hrs), and is considerably cheaper and easier to generate than for example $^{18}$F. Since SPECT does not rely on coincidence detection as does PET, the detector system is simpler and less expensive. The longer half life of $^{123}$I offers a longer time window for observation of the subjects, and often provides sufficient time for clearance of non-specific labelling where this is a problem. The resolution (7-8 mm) offered by recent generation SPECT scanners is close to that offered by PET (6 mm).

Cyclofoxy (6β-fluoro-3,14-dihydroxy-17-cyclopropyl methyl-4,5α-epoxymorphinan, U.S. Pat. No. 4,775,759) was the first ligand available for PET imaging of opioid receptors. Cyclofoxy has been used successfully to image and quantitate brain opioid receptors via PET technology. Several human neurological and psychiatric disorders have already been investigated with cyclofoxy. However, because of the disadvantages associated with PET technology, such investigations have been restricted only to major research centers. Two other PET ligands that recognize the opiate receptor, [$^{11}$C] carfentanyl and [$^{11}$C] diprenorphine have been used to label opioid receptors in humans. Their use has been similarly restricted to major research centers that have PET facilities.

To date, no other SPECT ligands for imaging opioid receptors has been developed for use in humans. Imaging opioid receptors with SPECT has the potential to go beyond imaging the brain. Recently, opioid receptors have been found on human lung cancer cells. As a result, by using N-substituted-6-iodo-3,14-dihydroxy-4,5-α-epoxymorphinans in SPECT lung scans, it may be possible to visualize the receptors on cancer cells that are the targets for chemotherapy, and thus be useful to assess therapeutic response to lung cancer treatments.

The present invention has been accomplished in order to find useful SPECT ligands suitable for imaging tissue which have the opioid receptors present both in vivo and in vitro. The ability to measure opioid receptors in vivo in their unaltered or native state offers considerable advantages over tissue homogenization techniques which often alter properties of the opioid receptors.

SUMMARY OF THE INVENTION

The present invention is directed to a radioimaging agent having the formula:

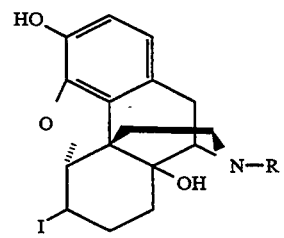

wherein I is selected from the group consisting of $^{123}$I and $^{125}$I; and where R is alkyl, cycloalkylloweralkyl or allyl.

The present invention is also directed to a method of radioimaging an opioid receptor which comprises contacting a tissue sample containing said opiate receptors with a sufficient amount of radioimaging agent to detect the presence of said opiate receptors having the above formula, and radio detecting the presence of said opioid receptor.

The radioimaging agent of the present invention is extremely desirable for imaging opioid receptors in vivo because it has a high ratio of specific to non-specific binding and allows the use of lower amounts of tracer to be given to the patients. This benefits the patients in two ways: a lower dose of radiation is administered and no untoward pharmacological effects can be expected to occur. In a typical SPECT imaging experiment, the patient would receive less radiation dose than a standard chest x-ray.

The radioimaging agent of the present invention is also extremely desirable for imaging opioid receptor binding in vitro since it can be used as a photoaffinity label for the opioid receptor and its subsequent characterization and purification as well as cell sorting after prelabeling the receptor with said ligands.

The present invention is also directed to a method of radioimaging opioid receptors which comprises contacting a tissue sample containing said opiate receptors with a sufficient amount of said radioimaging agent to detect the presence of any of said opiate receptors.

The method according to the present invention utilizes Single Photon Emission Computerized Tomography (SPECT), which procedure is well known in the art.

Another aspect of the invention is directed to a process for preparing empirically pure intermediates utilized in the synthesis of the above aforementioned radioimaging agents, and which have the formulas:

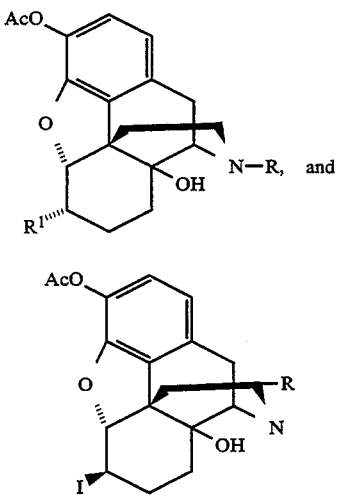

wherein R is alkyl, cycloalkylloweralkyl or allyl and $R^1$ is I or $CF_3SO_3$. The intermediate allows the synthesis and isolation of carrier free product having high specific antibody. This is extremely desirable when dealing with radio labeled compounds since, after separation, the labeled material will be composed of only the labeled material and not contain any unlabeled product or precursor material.

Moreover, according to the process of preparing the radioimaging agent of the present invention, no elimination products occur during the iodination step. During the preparation of cyclofoxy elimination products are present which is a considerable disadvantage since these elimination products are difficult to separate from cyclofoxy. The process of preparing the intermediate and radioimaging agent of the present invention does not result in elimination products.

By cycloalkylloweralkyl is meant a saturated cyclic hydrocarbon which has attached thereto a lower alkyl group of from 1 to 4 carbon atoms. The saturated cyclic hydrocarbon can be from a 3 to 6 membered ring. A preferred cycloalkylloweralkyl group is cyclopropylmethyl.

In defining R, alkyl means a saturated, straight or branched chain aliphatic hydrocarbon having from about 1 to 6 carbon atoms.

The radioimaging agent of the present invention can be administered alone or with a pharmaceutically acceptable carrier such as normal saline or sterile water for injection.

Titration of a suitable amount of the radioimaging agent of the present invention to be administered to a patient depends on the weight, age and health of the patient. An amount sufficient to detect the presence of opioid receptors ranges from 0.5 to 50 microcuries of radioimaging agent. In vitro binding assays would require not more than 1 microcurie of [$^{125}$I] ioxy, whereas a SPECT imaging study in humans would require up to 1 millicurie of [$^{123}$I] ioxy.

DETAILED DESCRIPTION OF THE PREFERRED EMBODIMENTS

The following example is directed to the synthesis of [$^{123}$I] and [$^{125}$I]-6$\beta$-iodo-3,14-dihydroxy-17-cyclopropylmethyl-4,5$\alpha$-epoxymorphinan, which utilizes naltrexone as the starting material.

The synthesis of an imaging agent where R=allyl would utilize the well known commercially available narcotic antagonist naloxone (Narcan ®); the reaction sequence and reagents would be identical to those for the synthesis of ioxy, infra.

The synthesis of radioimaging agents where R=cycloalkylloweralkyl or alkyl would require thebaine (readily available from natural sources) as the preferred starting material. Thebaine can be demethylated by well known and documented procedures to give northebaine. The northebaine can be transformed (by those skilled in the art) to N-alkylnorthebaine or N-cycloalkylloweralkylnorthebaine, which serve as precursors for the corresponding 6-$\beta$-iodo-3,14-dihydroxy-17-alkyl or 17-cycloalkylloweralkyl-4,5$\alpha$-epoxymorphinans.

EXAMPLE 1

Synthesis of [$^{123}$I] and [$^{125}$I]-6$\beta$-Iodo-3,14-Dihydroxy-17-Cyclopropylmethyl-4,5-$\alpha$-Epoxymorphinan Melting points were determined on a Thomas-Hoover capillary apparatus and are uncorrected. Specific rotation determinations at the sodium-D line were obtained in a 1 dm cell using a Perkin-Elmer 241-MC polarimeter (automatic). Gas chromatographic (GC) analysis was performed on a Hewlett-Packard 5880A instrument fitted with a 30 M SE-30 capillary column and a flame ionization detector. Elemental analyses were performed at Atlantic Microlabs, Atlanta, Ga. Chemical-ionization mass spectra (CIMS) were obtained using a Finnigan 1015 mass spectrometer. Electron ionization mass spectra (EIMS) and high resolution mass measurements (HRMS) were obtained using a VG-Micro Mass 7070F mass spectrometer. $^1$H-NMR spectra were obtained from $CDCl_3$ solutions using a Varian XL-300 spectrometer. Infra-red (IR) spectra were determined using a Beckman 4230 IR spectrophotometer; spectra were taken either from KBr pellets or $CHCl_3$ solutions. Thin layer chromatography (TLC) was performed on 250 $\mu M$ Analtech GHLF silica gel plates. TLC system A corresponds to $CHCl_3$-MeOH-conc. aq. $NH_3$ (90:9:1); TLC system B corresponds to $CHCl_3$-MeOH-conc. aq. $NH_3$ (80:18:2). All spectral ($^1$H-NMR, IR and Mass Spectral) data were consistent with the assigned structures.

The following is a general reaction scheme for the synthesis of Epimeric 6-iodo-6-deoxynaltrexones 1 and 2 with naltrexone (3) as the starting material.
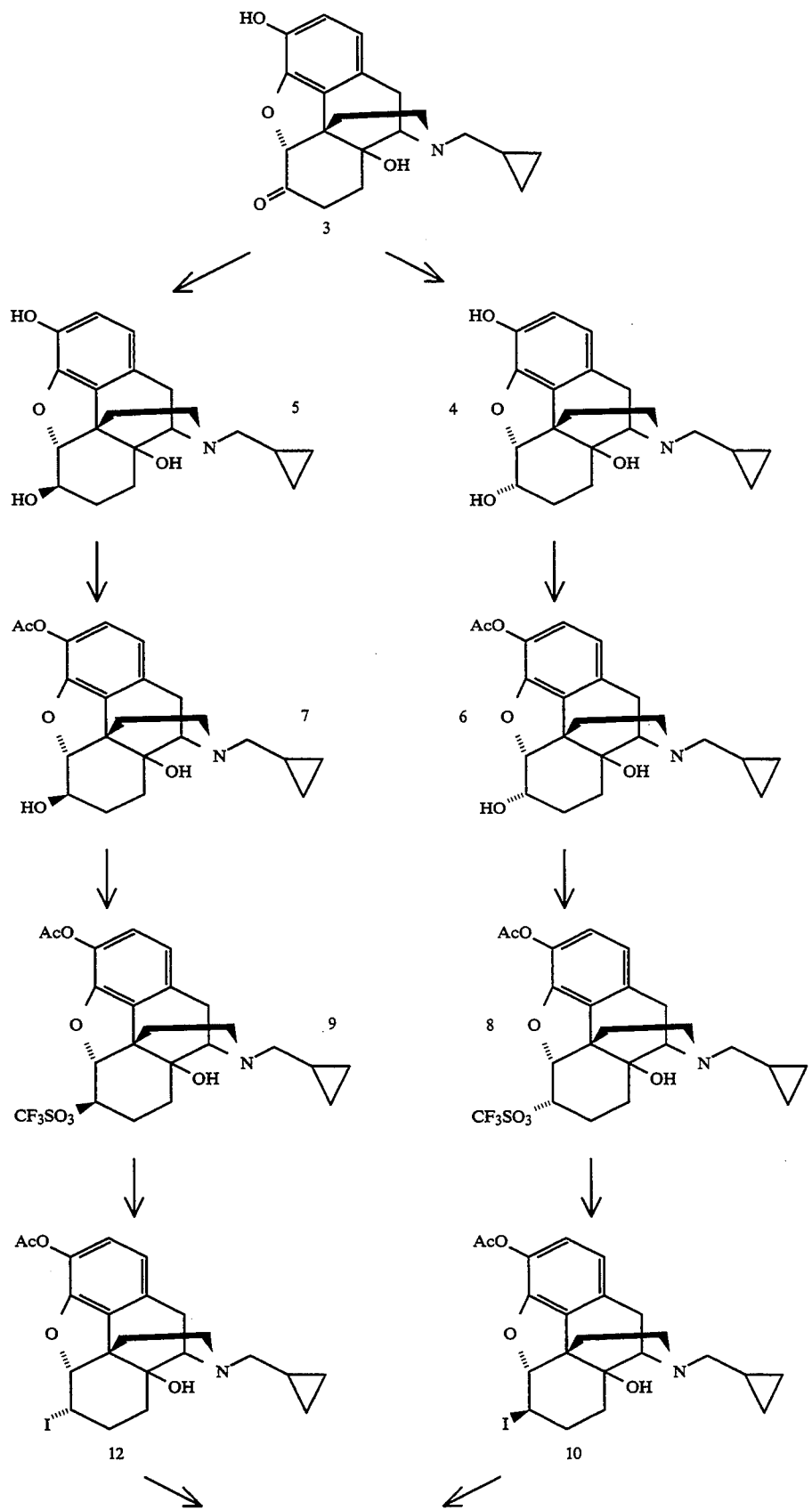

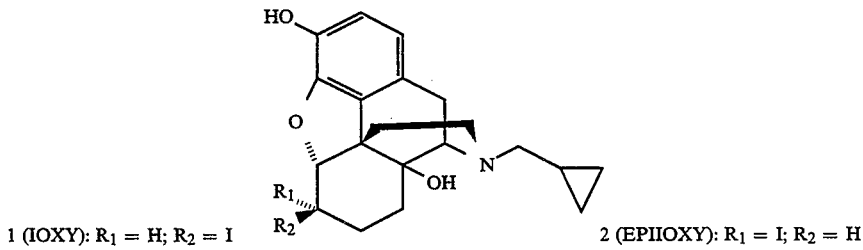

1 (IOXY): R₁ = H; R₂ = I  
2 (EPIIOXY): R₁ = I; R₂ = H

6α-Naltrexol(3,6α,14-Trihydroxy-17-Cyclopropyl-methyl-4,5α-Epoxymorphinan) (4)

To a stirred solution of naltrexone base 3 (21.6 g, 63.3 mmol) (Mallinckrodt Inc., St. Louis, Mo.), in dry THF (500 ml), at ambient temperature under argon, was added 14.5 ml of a 35% suspension of KH in mineral oil (126.6 mmol) and stirring was continued until the vigorous effervescence had subsided. The stirred solution was cooled to 5° C. and treated dropwise during 25 min. with 95 ml (95 mmol) of a 1.0M solution of K-Selectride (Aldrich) in THF, and stirred for 40 min. at 5° C. and then for 12 h at 25° C. The reaction was quenched by addition of 40 ml of water and the solvent was evaporated in vacuo. To the residue was added 400 ml of water and the aqueous mixture treated with concentrated aqueous HCl to pH 3–4. The acidic solution was extracted with ether (3×200 ml) and the ether extract discarded. Treatment of the aqueous layer with excess aqueous ammonia precipitated the free base. Extraction of the aqueous mixture with $CH_2Cl_2$ (3×100 ml), drying of the extract by passage through a short column of $Na_2SO_4$, and evaporation of the solvent in vacuo gave the crude product 21.7 g (quantitative) as a foam. Analysis of the mixture by TLC indicated the absence of epimeric (6β-) alcohol 5 in the reaction product. A small portion of the crude product was crystallized from acetonitrile to give base slightly contaminated with unreacted naltrexone: $[\alpha]_D = -202°$ (C. 0.735, $CHCl_3$). The total crude product (base) was dissolved in 150 ml of 2-propanol at 60° C. and treated with 9.63 g (63.3 mmol) of R(−)-mandelic acid. Crystallization occurred spontaneously on cooling to 25° C. The crystals were filtered and washed with 3×20 ml of cold (4° C.) 2-propanol followed by ether (20 ml) and dried in vacuo at 60° C. to afford 4.R(−)-mandelate: mp 163°–165° C., 23.6 g (75%) which was free of unreacted naltrexone. Anal. (calc for $C_{28}H_{33}NO_7 \cdot 0.75H_2O$): C 66.05, H 6.83, N 2.75; Found: C 66.12, H 6.86, N 2.69%. 4 (base): To a mixture of 4.R(−)-mandelate (22.58 g, 46.89 mmol), distilled water (200 ml) and $CHCl_3$ (200 ml) was added 1.87 g (46.89 mmol) of NaOH pellets or standardized 1.0M aqueous NaOH solution, and the mixture stirred for 10 min. at ambient temperature. The organic layer was separated and the aqueous layer was washed with 3×100 ml of $CHCl_3$ and the combined organic layer was dried through a plug of $Na_2SO_4$ and evaporated to give 4.(base) (quantitative) as a colorless foam. Crystallization from cold (5° C.) acetonitrile (100 ml) afforded 10.62 g of pure 4. Evaporation of the acetonitrile filtrate to 50 ml afforded a further 4.70 g of pure product: Anal. ( calc. for $C_{20}H_{25}NO_4$): C 69.95, H 7.34, N 4.08%; Found: C 69.76, H 7.37, N 3.99%. $[\alpha]_D = -214°$ (c 896, $CHCl_3$). mp 208°–209° C.

6β-Naltrexol (3,6β,14-Trihydroxy-17-Cyclopropylmethyl-4,5α-Epoxymorphinan) (5)

To a suspension of naltrexone base 3 (6.81 g, 20.0 mmol) (Mallinckrodt, St. Louis, Mo.), under argon was added 100 ml (enough to afford complete solution) of 0.533M aqueous NaOH. The alkaline solution of naltrexone was treated dropwise at ambient temperature during 20 min. with 8.64 g (80 mmol) of formamidinesulfinic acid dissolved in 200 ml of 0.533M aqueous NaOH. After the addition was complete, the solution was heated and stirred at 80°–85° C. for 1.5 h when TLC indicated the reaction to be complete. The reaction mixture was cooled (ice-bath) and then treated dropwise under argon with a solution of ammonium chloride (10.27 g, 192 mmol) in distilled water (100 ml). The aqueous mixture was extracted with 5×100 ml of $CHCl_3$ and the combined organic extract was filtered through a pad of $Na_2SO_4$ and evaporated in vacuo to afford crude 5.(base) as a foam which was dissolved in 20 ml of warm (50° C.) ethyl acetate and diluted to 60 ml with warm n-hexanes. Crystallization occurred spontaneously on cooling. The crystals were collected by filtration, washed with 2×10 ml of cold ethyl acetate/n-hexanes (1:3), and oven dried in vacuo at 60° C. to give 5 (6.11 g, 89%) (free of any 6α-epimer 4): $[\alpha]_D = -156°$ (c 0.604, MeOH). mp 707°–708° C.

3-Acetoxy-6β,14-Dihydroxy-17-Cyclopropylmethyl-4,5α-Epoxymorphinan (7)

5.(base) (5.50 g, 16.0 mmol) was suspended in 180 ml of distilled water, and to this was added 22.9 g (272.6 mmol) of $NaHCO_3$. To the vigorously stirred mixture in a 1000 ml beaker was added dropwise (care !), 13.7 ml of acetic anhydride. Voluminous effervescence and foaming occurred during the addition, and after 20 min., the reaction had subsided and a clear solution remained. The aqueous mixture was extracted with $CHCl_3$ (5×100 ml) and the organic extract was dried through a column of $Na_2SO_4$, and evaporated in vacuo to afford 7.(base) (quantitative) as an oil which failed to crystallize with a number of different salts.

3-Acetoxy-6α,14-Dihydroxy-17-Cyclopropylmethyl-4,5α-Epoxymorphinan (6)

4.(base) (12.00 g, 35.2 mmol) was treated with 50 g of $NaHCO_3$ and 30 ml of acetic anhydride as described above for 7 to afford 6 .base 13.5 g (quantitative) as a colorless oil. 6 (13.09 g) was treated with 3.09 g of oxalic acid in 100 ml of 1:1 acetone/2-propanol. After addition of the oxalic acid, copious crystallization occurred. The suspension of crystals was cooled to 4° C. and then filtered and washed twice with acetone-2-propanol (1:1) to afford 12.97 g of 6.oxalate.

3-Acetoxy-6α-Trifluoromethanesulfonyloxy-14-Hydroxy-17-Cyclopropylmethyl-4,5α-Epoxymorphinan (8)

To a solution of 6.(base) (11.65 g, 30.3 mmol) in 300 ml of alcohol free dry chloroform under argon was added 13.3 ml (121 mmol) of freshly redistilled N-methyl morpholine, and the solution was cooled to −30° C. To the cooled and stirred solution was added dropwise at such a rate that the temperature of the solution did not rise above −30° C., trifluoromethanesulfonic acid anhydride (10.2 ml, 60.5 mmol). The solution was stirred from −30° C. to −10° C. during 1 h and then 0° C. for 10 min. the reaction mixture was diluted with 300 ml of CHCl$_3$ and washed with 3×300 ml of saturated NaHCO$_3$ followed by 3×300 ml of water. Evaporation of the solvent afforded the crude product as an oil which was purified by flash column chromatography on silica gel eluting with 0.1:0.9:99 concentrated aqueous NH$_3$/MeOH/CHCl$_3$ to afford 12.75 g (81%) of 8.(base) as a colorless gum which was stored at −70° C. when not in use: $[\alpha]_D = -131°$ (c 1.405, CHCl$_3$).

3-Acetoxy-6β-Trifluoromethanesulfonyloxy-14-Hydroxy-17-Cyclopropylmethyl-4,5α-Epoxymorphinan (9)

To a stirred solution of 7.(base) (6.16 g, 16.0 mmol) and freshly redistilled N-methyl morpholine (7 ml, 64 mmol) in dry, alcohol free CHCl$_3$ at −30° C. was added trifluoromethanesulfonic acid anhydride (5.4 ml, 32 mmol) at such a rate that the temperature of the solution did not rise above −30° C. The solution was stirred from −30° C. to −20° C. for 10 min. and then diluted with 100 ml of CHCl$_3$. The reaction mixture was washed with 3×150 ml of saturated NaHCO$_3$, 3×150 ml of water, and the solvent evaporated in vacuo to afford the crude product as a dark oil. The crude product was purified by flash column chromatography on silica gel eluting with 0.2:1.8:98 concentrated aqueous NH$_3$/MeOH/CHCl$_3$, to afford pure 9.(base) (7.60 g, 92%) as a colorless gum. This could be crystallized from a mixture of ethyl acetate (5 ml) and hexanes (30 ml) at 4° C. Anal. ( calc. for C$_{23}$H$_{26}$F$_3$NO$_7$S ) C 53.38, H 5.06, N 2.71%; Found C 53.18, H 5.09, N 2.26% $[\alpha]_D = -128°$ (c 1.262, CHCl$_3$).

3-Acetoxy-6β-Iodo-14-Hydroxy-17-Cyclopropylmethyl-4,5α-Epoxymorphinan (10)

To a stirred solution of 8.(base) (9.16, 17.7 mmol) in dry acetonitrile (300 ml) at −10° C. under argon was added (in one portion), tetraethylammonium iodide (9.11 g, 35.4 mmol) and the solution stirred at −10° C. for 1 h, and then at 25° C. for 3 h. The solvent was evaporated at ambient temperature in vacuo, and the colorless residue was dissolved in 500 ml of CHCl$_3$ and washed with water (4×100 ml). Evaporation of the solvent afforded 10.(base) (7.90 g, 90%) as a crystalline solid. The residue was dissolved in 25 ml of warm ethyl acetate and the solution was diluted by the addition of 60 ml of warm n-hexane. Crystallization occurred spontaneously as the solution cooled. When the temperature of the mixture had reached ambient temperature, further crystallization was achieved by allowing the crystallization mixture to stand at 4° C. for 2 h. The crystals were filtered off and washed with cold (0° C.) solvent, yield 6.00 g (68%):$[\alpha]_D = -236°$ (c 1.126, CHCl$_3$). Anal. (calc. for C$_{22}$H$_{26}$INO$_4$): C 53.34, H 5.29, N 2.83%; Anal found: C 53.19, H 5.35, N 2.81%.

3-Acetoxy-6α-Iodo-14-Hydroxy-17-Cyclopropylmethyl-4,5α-Epoxymorphinan (12)

A mixture of 9.(base) (3.00 g, 5.80 mmol) and tetraethylammonium iodide (2.98 g, 11.6 mmol) in dry acetonitrile (50 ml) was heated and stirred for 4 h at 80° C. under an argon atmosphere when TLC (0.1:0.9:99 concentrated aqueous NH$_3$MeOH/CHCl$_3$) and mass spectral analysis indicated that the reaction was complete. The solvent was evaporated in vacuo and the residue was dissolved in CHCl$_3$ (100 ml) washed with 4×40 ml of water and evaporated to give 12.(base) as an oil, 2.89 g (97%). Recrystallization from 10 ml of warm 2-propanol afforded 2.22 g (77%) of pure 12:$[\alpha]_D = -244°$ (c 0.625, CHCl$_3$). Anal. (calc. for C$_{22}$H$_{26}$INO$_4$); C 53.34, H 5.29, N 2.83%; Anal found: C 53.44 , H 5.33 , N 2.81%.

6β-Iodo-3,14-Dihydroxy-17-Cyclopropylmethyl-4,5α-Epoxymorphinan (1) (ioxy)

10.(base) (5.00 g, 10.1 mmol) was dissolved in a mixture of THF (70 ml) and MeOH (70ml) and the mixture was treated with concentrated aqueous ammonia solution and stirred for 25 min. under an argon atmosphere at ambient temperature when TLC (1:9:90 concentrated aqueous NH$_3$/MeOH/CHCl$_3$) indicated complete reaction. The solvent was evaporated in vacuo and the residue was dried under high vacuum to afford a quantitative yield of 1.(base) as a white powder. 1.oxalate was crystallized from 150 ml of boiling 2-propanol and dried in vacuo at 80° C. to afford 5.47 g (quantitative) yield of 1.oxalate: $[\alpha]_D = -149°$ (c 1.179, MeOH) mp 177°(dec). Anal. (calc. for C$_{22}$H$_{26}$INO$_7$.C$_3$H$_8$O): C 49.75, H 5.68, N 2.32%; Anal. found: C 49.39, H 5.30, N 2.35%.

6α-Iodo-3,14-Dihydroxy-17-Cyclopropylmethyl-4,5α-Epoxymorphinan (2) (Epiioxy)

10.(base) (1.90 g, 3.84 mmol) in a mixture of 40 ml of MeOH and 20 ml of THF was treated with concentrated aqueous ammonia solution and stirred for 25 min. under an argon atmosphere at ambient temperature when TLC (1:9:90 concentrated aqueous NH$_3$/MeOH/CHCl$_3$) indicated complete reaction. The solvent was evaporated in vacuo and the residue was dried under high vacuum to afford a quantitative yield (1.74 g) of 2.(base). The oxalate salt was crystallized from 50 ml of 2-propanol. The solution was cooled to 25° C. and the crystals were filtered and washed with 2×10 ml of cold (0° C.) 2-propanol followed by ether (10 ml). Yield (after drying overnight in vacuo) at 80° C.=2.06 g (99%).$[\alpha]_D = -153°$ (c 0.868, MeOH) mp 211°-212° C. (dec) . Anal. (calc. for C$_{22}$H$_{26}$INO$_7$.C$_3$H$_8$O): C 49.75, H 5.68, N 2.32; Anal. found: C 49.47, H 5.61, N 2.29.

Preparation of [$^{125}$I]3-Acetoxy-6β-Iodo-14-Hydroxy-17-Cyclopropylmethyl-4,5α-Epoxymorphinan ([$^{125}$I]3-O-Acetylioxy) (λ$^{125}$I]10)

An aqueous solution of [$^{125}$I] sodium iodide (4 mCi, 2200. Ci/mmol) was carefully evaporated under a stream of nitrogen gas, and the residue remaining was dissolved in acetonitrile (100 μl containing 100 μg of precursor 8). The solution was heated to 64° C. for 60 min. under a nitrogen atmosphere. The reaction mixture was diluted to 5 ml with distilled water and passed through a $C_{18}$-SepPak (Waters Associates) (Milford, Mass.). The SepPak was washed with $3\times 10$ ml of water to remove unreacted [$^{125}$I] sodium iodide. The unreacted precursor 8 and [$^{125}$I]3-O-acetyl ioxy ([$^{125}$I]-10) were eluted with $2\times 0.5$ ml of acetonitrile containing 0.1% trifluoroacetic acid (TFA). Counting of the product on a gamma counter (Capintec, Model CRC10 Radioisotope Calibrator, Capintec Inc.) indicated a yield of 1.38 mCi (34.5% incorporation of carrier-free $^{125}$I). The acetonitrile/TFA solvent was removed by careful evaporation under a stream of nitrogen and the residue was redissolved in 1:3 (0.1% aqueous TFA/acetonitrile) and injected into a HPLC machine (Waters Associates) fitted with a $C_{18}$ reverse phase cartridge column ($0.4\times 10$ cm; 3 μm particle size). Elution was isocratic at a flow rate of 0.9 mi/min. Under these conditions, 3-O-acetylioxy eluted at 13 min and the UV absorbance trace (measured at 214 nM) returned to baseline prior to the precursor 8 eluting at 19 min. The radiolabelled peak displayed the exact retention time and elution profile as unlabelled 3-O-acetylioxy (10).

An alternative set of reaction conditions were investigated: Carrier-free aqueous [$^{125}$I] sodium iodide (5 mCi) was dried down by evaporation under a stream of nitrogen and reconstituted with 40 μL of dry acetonitrile. To this solution was added triflate ester 8 (100 μg) dissolved in 10 μL of dry acetonitrile and the reaction mixture was heated to 76° C. for 1.5 h under a nitrogen atmosphere. The reaction mixture was worked up as described above to give 5.0 mCi (quantitative) of carrier-free [$^{125}$I]ioxy-3-O-acetyl ester ([$^{125}$I]10).

The radiolabelled products were stored at −20° C. and used within 1 week of purification. The material was dried down under a gentle stream of nitrogen and redissolved in normal saline prior to intravenous (IV) injection into rats (300 g, male Sprague-Dawley) in a volume of 100 μl/100 g body weight.

[$^{125}$I]6μ-Iodo-3,14-Dihydroxy-17-Cyclopropylmethyl-4,5(X-Epoxymorphinan ([$^{125}$I]ioxy) ([$^{125}$I]1)

Cleavage of the 3-O-acetyl group of [$^{125}$I]3-O-Acetylioxy ([$^{125}$I]10) was performed starting with 315 μCi of [$^{125}$I]3-O-Acetylioxy dissolved in 50 μl of acetonitrile. To this solution at 25° C. was added 50 μl of concentrated aqueous ammonia solution and the reaction mixture was allowed to stand at 25° C. for 20 min. The reaction solvent was removed by careful evaporation under a stream of nitrogen. The residue was dissolved in 50 μl of 0.1% aqueous TFA/acetonitrile and purified by HPLC as described above for [$^{125}$I]3-O-Acetylioxy to give [$^{125}$I]1 (279 μCi, 88.5% yield). The HPLC profile of the reaction product indicated that complete cleavage of the 3-O-acetyl group had occurred within 20 min after addition of the ammonia solution. The [$^{125}$I]ioxy eluted with the exact elution profile of unlabelled ioxy(1). The product was stored at −20° C. and used within 1 week of purification. The material was dried down under a gentle stream of nitrogen and redissolved in normal saline prior to intravenous (IV) injection into rats (300 g, male Sprague-Dawley) in a volume of 100 μl/100 g body weight.

X-Ray Crystallographic Analysis of 3-Acetoxy-6p-Iodo-14-Hydroxy-17-Cyclopropylmethyl-4,5(X-Epoxymorphinan (10)

Crystals of 10, $C_{22}H_{26}NO_4I$, FW=495.3 were grown by slow cooling of a solution of 10 in 3:7 ethyl acetate/n-hexane. A clear $0.34\times 0.40\times 0.48$ mm crystal was selected for data collection. Data were collected on a computer controlled diffractometer with an incident beam graphite monochromator (Nicolet R3m/V with Mo Kα radiation, λ=0.71073 Å, T=295K). A least-squares refinement using 25 centered reflections within $50<2\theta<80^0$ gave the triclinic P1 cell a=6.994 (2), b=8.513(2), c=9.660(2) Å, α=64.22(2), β=83.28(2), and γ=89.06(2)$^0$, with V=513.9(2) Å$^3$, Z=1, and $d_{calc}$=1.60 g/cm$^3$. A total of 2954 independent reflections were measured in the θ/2θ mode to $2\theta_{max}$=55°. Corrections were applied for Lorentz and polarization effects. A semi-empirical absorption correction based on the ρ-dependence of 12 reflections with χ ca. 90° was applied, μ=1.57 mm$^{-1}$, and maximum and minimum transmission was 0.92 and 0.75, respectively. The structure was solved by direct methods with the aid of the program SHELXTL and refined with a full matrix least-squares according to Sheldrick, G.M., Minicomputer Programs for Structure Determination, University of Gottingen, Sweden, 1980. The 273 parameters refined include the coordinates and anisotropic thermal parameters for all non-hydrogen atoms. Carbon hydrogens using a riding model in which the coordinate shifts of the carbon atoms were applied to the attached hydrogen atoms, and C-H=0.96 Å, H angles idealized and $U_{iso}(H)=1.2.U_{eq}(C)$, except for those on the cyclopropylmethyl group and the hydroxyl hydrogen which were refined isotropically. The final R-value for the 2811 (includes c.a. 200 Friedel pairs) observed reflections with Fo>3σ(lF$_o$l) where R=0.027, and wR=0.035, where $W=1/[\sigma^2(lF_ol)+g(F_o)^2]$ and g=0.00023. The goodness of fit parameter was 1.71 and final difference Fourier excursions were 0.30 and −0.97 eÅ$^{-3}$.

The absolute configuration determination was based on the method suggested by D. Rogers *Acta Cryst* 1981, A37, 734–741. The parameter η which multiplies all ΔF" values (imaginary component of atomic scattering factor) refines to a value of η=1.03(4). A correct choice of enantiomer would give +1.0 and an incorrect choice −1. In addition, the wR for the choice of the other enantiomer is 0.049, significantly above that of the correct hand.

EXAMPLE 2

BIOLOGICAL STUDIES

Biological Methods In Vivo Antagonist Activity

Assessment of the ability of compounds 1, 2 and 10, 12 to cross the blood brain barrier was tested in male Sprague-Dawley rats (300 g) acutely treated with morphine. It was expected that these ligands would have antagonist activity and determined whether they could reverse morphine-induced analgesia. A baseline paw withdrawal to a radiant thermal stimulus was obtained in unrestrained animals as described in Iadarola et al., *Brain Res.* 1988, 455, 205–212 and Hargreaves, *Pain* 1988, 32, 77–78. The stimulus was set to give a baseline withdrawal latency of approximately 10 sec. and the cutoff was at 18 sec. After baseline testing, morphine sulphate, 10 mg/kg, was injected subcutaneously in a volume of 0.1 ml of saline/100 g of body weight. By 40 min., the rats were fully analgesic, most reached the 18 sec. cutoff, and showed obvious behavioral signs of opioid effect. Naltrexone and the 3-O-acetylated [(10) and (12)] and deacetylated [(1) and (2)] ioxy epimers were administered intravenously (5 mg/kg each, in 0.1 ml saline/100 g body weight). The behavioral arrest and other opioid effects were reversed in a matter of seconds by all of the ioxy and epiioxy derivatives as with naltrexone. Withdrawal latency, tested within 5–10 min. of the i.v. injection, returned to near baseline values in all cases. The reversal lasted for at least 40 min.

Receptor Binding

Mu binding sites were labeled using 1.7 nM [$^3$H]DAGO (SA=40.8 Ci/,mmol) and rat lysed-P2 membranes as previously described (Rothman et al., J. Pharmacol. Exp. Ther., 1988, 247, 405–416). Briefly, incubations proceeded for 4–6 hrs. at 25° C. in 50 mM Tris-HCl pH 7.4, containing a protease inhibitor cocktail (bacitracin {100 μg/ml}, bestatin {10 μg/ml}, leupeptin {4 μg/ml} and chymostatin {2 μg/ml}). Nonspecific binding was determined using 20 μM levallorphan. Higher affinity ($\delta_{cx}$) delta binding sites were labeled using 1.9 nM [$^3$H][D-ala$^2$, D-leu$^5$]enkephalin (SA=30 Ci/mmol) and rat lysed-P2 membranes as previously described (Rothman et al., Neuropeptides 1988, 11, 13–16). Briefly, incubations proceeded for 4–6 hrs. at 25° C. in 10 mM Tris-HC, pH 7.4, containing 100 mM choline chloride, 3 mM MnCl$_2$, and the protease inhibitor cocktail. 100 nM MeTyr-D-Ala-Gly-N(Et)-CH(CH$_2$-Ph)CH$_2$-N(CH$_3$)$_2$ (LY164929) was used to block binding to the $\delta_{cx}$ binding site, and 100 nM [D-pen$^2$, L-pen$^5$]enkephalin was used to block binding to the $\delta_{ncx}$ binding site. Nonspecific binding was determined using 20 μM levallorphan. [$^3$H]cycloFOXY binding sites (μ plus κ$_2$) were labelled using 1.3 nM [$^3$H]cycloFOXY (SA=20.6 Ci/mmol) and rat brain lysed-P2 membranes as previously described (Rothman et al. J. Biol. Psych. 1988, 23, 435–458). Nonspecific binding was determined using 20 μM levallorphan. κ$_1$ binding sites were labelled using 1.8 nM [$^3$H]U69,593 (SA=40 Ci/mmol) and guinea pig brain membranes depleted of μ and δ binding sites by pretreatment with 2-(4-ethoxybenzyl)-1-diethylaminoethyl-5-isothiocyanato-benzimidazole HCl (BIT) and N-phenyl-N-[1-(2-(4-isothiocyanato)phenethyl)-4-piperidinyl]propanamide HCl (FIT) as previously described (Rothman et al. Peptides, 1990, 11, 311–331), except that the incubation temperature was at 25° C. Briefly, incubations proceeded for 4 to 6 hrs. at 25° C. in 50 mM Tris-HCl pH 7.4, containing the protease inhibitor cocktail plus 1 μg/ml captopril. Nonspecific binding was determined using 1 μM U69,593. κ$_2$ binding sites were labelled with 1.8 nM [$^3$H]bremazocine using guinea pig brain membranes depleted of μ and δ binding sites by pretreatment with BIT and FIT, as previously described (Rothman et al. Peptides, 1990, 11, 311–331.) Briefly, incubations proceeded for 4 to 6 hrs. at 0° C. in 50 nM potassium phosphate buffer, pH 7.4, with the same protease inhibitor cocktail used for the [$^3$H]U69,593 binding assay. Nonspecific binding was determined with 1 μM (−)-bremazocine. Each [$^3$H]ligand was displaced by 8 concentrations of test drug. The data of two experiments were combined and fit to the two parameter logistic equation (Rodbard et al. Clin. Chem. 1976, 22, 350–358) for the best-fit estimates of the IC$_{50}$ and the slope factor. The K$_i$ values were calculated using the equation K$_i$ =IC$_{50}$/(1+[L]/K$_d$). The K$_d$ values of the respective ligands were as follows: [$^3$H]DAGO (0.7 nM), [$^3$H][D-ala$^2$, D-leus$^5$]enkephalin (1.6 nM at the $\delta_{ncx}$ site, 12.2 nM at the $\delta_{cx}$ site), [$^3$H]U69,593 (1.6 nM), [$^3$H]bremazocine (1.0 nM), [$^3$H]cycloFOXY (0.8 nM).

Ioxy (1) and epiioxy (2) were evaluated in rat and guinea pig brain membranes for their opiate receptor selectivity and potency. The antagonist properties of 1, 2 and acetate esters 10 and 12 were evaluated in vivo using the rat paw withdrawal latency test (Iadarola et al. Brain Res. 1988, 455, 205–212 and Hangreaves, Pain, 1988 32, 77–78) and indicated all the compounds (1, 2, 10 and 12), like naltrexone, could produce a complete reversal of the effects of morphine. The results of this in vivo study also indicated that the compounds were getting into the brain which is especially of importance in the development of SPECT or PET scanning ligands for brain receptor imaging in rats. The acetate esters 10 and 12 produced more potent effects on morphine induced paw withdrawal latency than their corresponding phenolic counterparts indicating that they penetrated the blood brain barrier more effectively by virtue of their increased lipophilicity relative to the desacetyl compounds 1 and 2; the result indicated that 10 and 12 served as prodrug forms of 1 and 2. The combined in vivo and in vitro data indicate that of the compounds tested, those with the 6β-configuration were generally more potent opioid antagonists than those with the 6α-configuration, i.e., ioxy is more effective than epiioxy. This comparison was not made during development of the $^{18}$F cyclofoxy compounds.

TABLE 1

| Opiate Receptor Subtype Selectivity of Iodinated Opiates | | | |
|---|---|---|---|
| IC$_{50}$ (nM) | N | r$^2$ | K$_i$ (nM) |
| μ and κ$_2$ Receptor Binding | | | |
| [$^3$H]CycloFOXY (K$_d$ = 0.8 nM; ligand Concentration = 1.3 nM) | | | |
| IOXY       0.77 ± 0.05 | 0.99 ± 0.06 | 0.99 | 0.29 |
| EpiIOXY    4.34 ± 0.19 | 1.21 ± 0.06 | 0.99 | 1.65 |
| CycloFOXY  8.98 ± 0.35 | 1.18 ± 0.05 | 0.99 | 3.42 |
| Naltrexone 6.77 ± 0.18 | 1.11 ± 0.03 | 0.99 | 2.57 |
| CycloBROXY 3.14 ± 0.11 | 1.04 ± 0.04 | 0.99 | 1.19 |
| High Affinity δ Receptors | | | |
| [$^3$H] DADLE (K$_d$ = 1.6 nM; ligand concentration = 1.9 nM) | | | |
| IOXY       5.6 ± 3.1  | 0.77 ± .07 | 0.98 | 11.7 |
| EpiIOXY    101 ± 8.4  | 0.99 ± .07 | 0.99 | 46.2 |
| CycloFOXY  268 ± 33   | 0.87 ± .09 | 0.97 | 122 |
| Naltrexone 221 ± 31   | 0.77 ± .08 | 0.97 | 101 |
| CycloBROXY 4.30 ± .46 | 0.99 ± .09 | 0.98 | 1.96 |
| Low Affinity δ Receptors | | | |
| [$^3$H] DADLE (K$_d$ = 12.2 nM: Ligand concentration = 2.1 nM) | | | |
| IOXY       2.64 ± .21 | 0.76 ± .05 | 0.99 | 2.25 |
| EpiIOXY    8.06 ± .58 | 0.94 ± .06 | 0.99 | 6.88 |
| CycloFOXY  16.2 ± 0.8 | 0.76 ± .03 | 0.99 | 13.8 |
| Naltrexone 5.57 ± .31 | 0.94 ± .05 | 0.99 | 4.75 |
| CycloBROXY 5.77 ± .14 | 0.83 ± .02 | 0.99 | 4.92 |
| κ$_2$ Receptor Binding | | | |
| [$^3$H] BRM (K$_d$ = 1.0 nM; ligand concentration = 1.8 nM) | | | |
| IOXY       7.65 ± .23 | 0.74 ± .02 | 0.99 | 2.73 |
| EpiIOXY    23.7 ± 1.1 | 0.76 ± .03 | 0.99 | 8.46 |
| CycloFOXY  66.0 ± 3.9 | 0.90 ± .05 | 0.99 | 23.5 |
| Naltrexone 47.2 ± 1.9 | 0.74 ± .02 | 0.99 | 16.8 |
| CycloBROXY 20.2 ± 1.2 | 0.55 ± .02 | 0.99 | 7.21 |
| κ$_1$ Receptor Binding | | | |
| [$^3$H] U69,593 (K$_d$ = 1.6 nM; ligand concentration = 1.8 nM) | | | |
| IOXY       0.89 ± .01 | 1.04 ± .02 | 0.99 | 0.42 |
| EpiIOXY    3.17 ± .06 | 1.10 ± .02 | 0.99 | 1.49 |
| CycloFOXY  7.88 ± .09 | 0.94 ± .09 | 0.99 | 3.71 |
| Naltrexone 5.97 ± .24 | 0.99 ± .04 | 0.99 | 2.81 |
| CycloBROXY 0.70 ± .02 | 1.03 ± .03 | 0.99 | 0.32 |
| μ Recptor Binding | | | |
| [$^3$H] DAGO (K$_d$ = 0.7 nM; ligand concentration = 1.7 nM) | | | |
| IOXY       2.74 ± .21 | 1.05 ± .07 | 0.99 | 0.80 |
| EpiIOXY    7.16 ± .72 | 0.95 ± .08 | 0.99 | 2.09 |
| CycloFOXY  11.4 ± .05 | 1.13 ± .05 | 0.99 | 3.32 |
| Naltrexone 4.04 ± .15 | 0.99 ± .04 | 0.99 | 1.18 |
| CycloBROXY 4.21 ± .14 | 1.05 ± .04 | 0.99 | 1.23 |

In vitro studies in the rat brain homogenates (Table 1) against [$^3$H]cycloFOXY (a measure of $\mu$ and $\kappa_2$ receptor binding (Rothman et al. Neuropeptides 1988, 12, 181–187 and Rothman et al. Biol. Psych. 1988, 63, 435–458), ioxy (1) exhibited a $K_i$ of 0.29 nM. However, epiioxy (2) exhibited a $K_i$ of 1.65 nM or a 6-fold reduction in affinity. This surprisingly indicates that for $\mu$ and kappa opioid receptor binding, the 6$\mu$-configuration has unexpectedly greater activity than the 6$\alpha$-configuration. CycloFOXY containing the smaller 6$\beta$-fluorine atom exhibited a 12-fold lower affinity compared with 1 which indicates that the larger more polarizable iodine atom is beneficial to its opioid receptor binding interaction. This is further exemplified with the 6$\beta$-bromo analog (Newman, A.H. et al. unpublished results), of 1 (cyclobroxy) which shows an intermediate receptor affinity (1.19 nM). Also, unexpectedly, compound 1 was also more potent than the opiate antagonist, naltrexone (Ki=2.57 nM).

An analogous series of results (to those seen with displacement of [$^3$H]cycloFOXY) was observed for in vitro potency of these compounds at the high affinity δ-site ([$^3$H]DADLE), Rothman et al., Neuropeptides, 1988, 11, 13–16, in the rat (Table 1). Thus, ioxy (1) exhibited an affinity of 11.7 nM while epiioxy exhibited a 4-fold lowered affinity ($K_i$=46.2 nM). As for displacement of [$^3$H]cycloFOXY, cycloFOXY was also approximately 10-fold less potent than 1 for displacement of [$^3$H]DADLE from the high affinity δ-site. Naltrexone exhibited comparable affinity while cycloBROXY displaced [$^3$H]DADLE with a 6-fold higher affinity.

For displacement of [$^3$H]DADLE from the low affinity δ-site, Rothman, 1988, supra, ioxy (1) exhibited the highest affinity of all the compounds tested in Table 1. Epiioxy showed a 3-fold lower affinity ($K_1$=6.88 nM) and cycloFOXY showed a 6-fold lower affinity, again corroborating the beneficial effect of the larger iodine atom and 6$\beta$-configuration on opioid receptor binding as seen above.

In guinea pig membranes pretreated with the site directed affinity ligands 2-(4-ethoxybenzyl)-1-diethylaminoethyl-5-isothiocyanatobenzimidazole (BIT) and N-phenyl-N-[1-(2-(4-isothiocyanato)phenethyl)-4-piperidinyl]propanamide, (Rice et al., Science 1983, 220, 314–316), (FIT), to irreversibly deplete $\mu$-and δ-sites, respectively, the displacement of the non-selective opioid, [$^3$H]bremazocine ([$^3$H]BRM) is a measure of $\kappa_2$-receptor binding affinity, (Rothman et al., Peptides, 1990, 11, 311–331 and Rothman et al., Neuropeptides, 1985, 6, 503–515). Thus, (Table 1), ioxy displaced [$^3$H]BRM with a $K_i$ of 2.73 nM while epiioxy (2) was 3-fold less potent in this respect. CycloFOXY containing the smaller F-atom was less potent by a factor of 7–9 fold. Naltrexone was 7-fold less potent and cycloBROXY was 3-fold less potent.

[$^3$H]U69,593 displacement from guinea pig membranes pretreated with the site directed affinity ligands BIT, Rice et al., 1983, supra, and FIT (to deplete $\mu$-and δ-receptors, respectively) is a good measure of $\kappa_1$-receptor binding affinity, Rothman et al., 1983, supra. Of the compounds tested (Table 1), ioxy ($K_i$=0.42 nM) and cycloBROXY ($K_i$=0.32 nM) were the most potent displacers of [$^3$H]U69,593 under these conditions. Epiioxy (2) was 4-fold less potent while cycloFOXY was 9-fold less potent (as it was for $\kappa_2$-receptors). Similarly, naltrexone was 7-fold less potent.

Displacement of [$^3$H]DAGO (Table 1) from rat brain membranes is a versatile measure of $\mu$-receptor binding affinity, Rothman et al., Pharmacol, Exp. Ther., 1988, 247, 405–416. Among all of the compounds tested at this receptor, ioxy was the most potent. Its epimer (2) showed a 2-fold lower affinity, and cycloFOXY was 4-fold less potent. Naltrexone and cycloBROXY were both about 1.5-fold less potent at this site.

Based on both in vivo and in vitro opioid receptor potency, ioxy was selected instead of epiioxy for radioiodination. In the radioiodination experiments, the tetraethylammonium iodide that was used in the unlabelled work was substituted with sodium $^{125}$iodide. The conditions employed utilized anhydrous carrier-free Na$^{125}$I in dry acetonitrile. Non-optimized conditions (64° C. for 10 h) gave a 34.5% radiochemical yield of [$^{125}$I]10. Optimization of the conditions (76° C. for 1.5 h) resulted in a quantitative yield of [125I]10. As with unlabelled 10, deprotection of the 3-O-acetyl group occurred smoothly in the presence of excess concentrated aqueous ammonia/acetonitrile to give the desired [$^{125}$I]1 in 88.5% radiochemical yield after HPLC purification on an analytical scale reverse phase (C18) cartridge column.

Preliminary in vivo labelling experiments using both [$^{125}$I]1 and [$^{125}$I]10 indicated that they could label opiate rich areas of rat brain as determined by autoradiography.

The in vivo experiments unexpectedly proved that ioxy (compound 1) is a potent opioid receptor antagonist in the rat. The experiments demonstrated that it readily passed the blood brain barrier. Ioxy was unexpectedly more potent in vivo than compound 2 and cyclofoxy as seen in Table 1 at all of the opioid receptor subtypes. A qualitative examination of atom size in the 6-position versus receptor potency indicated that I>Br>F. Ioxy exhibited a greater degree of kappa selectivity ($\kappa_1/\mu$=1.9) ($\kappa_2/\mu$=0.3) than cycloFOXY ($\kappa_1/\mu$=0.89) ($\kappa_2/\mu$=0.14).

A combination of both receptor binding data and in vivo potency (after iv administration) of 1 and 10 together with preliminary in vivo receptor localization experiments with [$^{125}$I]1 and [$^{125}$I]10 strongly indicate that the $^{123}$I-labelled versions of these compounds will be suitable for SPECT labelling of opioid receptors in living subjects.

EXAMPLE 3

SPECT Protocol

The test dosage of radioactivity for these studies is 10 mCi of [$^{123}$I]-labeled ioxy. The preparation of the injection material (i.e. sterilization, final calibration of dosage and loading the syringe) is done in a radiopharmacy. A Rhesus monkey is anesthetized by inhalation Metophane and an intravenous catheter implanted for injection of radiolabeled ioxy and transported to the SPECT suite. Prior to injection of the radioactive tracer the thyroid is blocked by injection of potassium iodide. The animal is maintained under anesthesia for the duration of the procedure. The monkey's head is placed in a custom-designed animal-sized collimator for the scan and data is obtained continuously for 120 minutes following an intravenous bolus of [$^{123}$I]-labeled ioxy. Specificity of the binding to the monkey opiate receptor is tested by examining the stereospecific displacement of the labeled tracer using intravenous injection of (+)- or (−)-naloxone. This test is performed at approximately the peak of receptor occupancy. Following the completion of the scan the monkey is kept in a containment facility until the radioactive material is clear from the system.

The use of these compounds in basic animal studies, biochemical studies and in clinical human studies will advance knowledge of the endogenous opioid system in normal and disordered brain function and possibly in the function of the endocrine and reproductive systems and in cancer biology and chemotherapy.

Having thus described the invention, it will be obvious that the same can be modified without departing from the spirit and scope thereof.

We claim:

1. A method of radioimaging opioid receptors which comprises contacting a tissue sample containing said opiate receptors with a sufficient amount of radioimaging agent having the formula

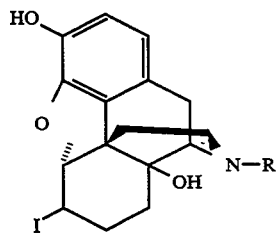

wherein I is selected from the group consisting of $^{123}$I and $^{125}$I; and where R is alkyl having from about 1 to 6 carbon atoms, cycloalkylloweralkyl or allyl to detect the presence of any of said opiate receptors; and radio detecting the presence of said opioid receptors.

2. The method according to claim 1, wherein in said compound, I is $^{123}$I.

3. The method according to claim 1, wherein in said compound, I is $^{125}$I.

4. The method according to claim 1, wherein said tissue sample is detected in vitro.

5. The method according to claim 1, wherein said tissue sample is detected in vivo.

6. The method according to claim 1, wherein said radiodetection is Single Photon Emission Computerized Tomography (SPECT).

7. A compound having the formula:

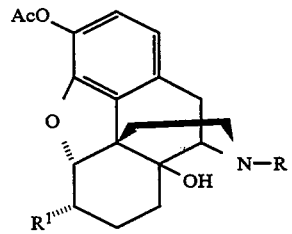

wherein $R^1$ is I; and R is alkyl having from 1 to 6 carbon atoms, cycloalkylloweralkyl or allyl.

8. The compound according to claim 7,

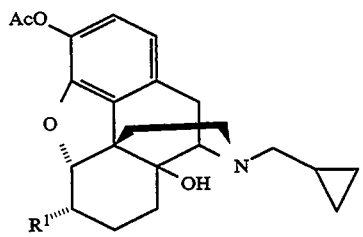

wherein $R^1$ is I.

* * * * *